United States Patent
Kim et al.

(10) Patent No.: US 10,264,904 B1
(45) Date of Patent: Apr. 23, 2019

(54) ANTI-TREMOR UTENSIL

(71) Applicants: Dongho Kim, New York, NY (US); Kwanwoo Yoon, New York, NY (US)

(72) Inventors: Dongho Kim, New York, NY (US); Kwanwoo Yoon, New York, NY (US)

(*) Notice: Subject to any disclaimer, the term of this patent is extended or adjusted under 35 U.S.C. 154(b) by 0 days.

(21) Appl. No.: 15/641,584

(22) Filed: Jul. 5, 2017

Related U.S. Application Data (60) Provisional application No. 62/359,925, filed on Jul. 8, 2016.

(51) Int. Cl.
*A47G 21/08* (2006.01)
*A47G 21/04* (2006.01)
*A47G 21/02* (2006.01)

(52) U.S. Cl.
CPC ............. *A47G 21/08* (2013.01); *A47G 21/02* (2013.01); *A47G 21/04* (2013.01)

(58) Field of Classification Search
CPC ......... A47G 21/08; A47G 21/02; A47G 21/04
See application file for complete search history.

(56) References Cited

U.S. PATENT DOCUMENTS

| | | | | |
|---|---|---|---|---|
| 4,237,873 A | * | 12/1980 | Terry | A61F 5/013 602/20 |
| 4,964,264 A | * | 10/1990 | Adams | A01K 13/006 119/850 |
| 5,058,571 A | * | 10/1991 | Hall | A63B 23/12 601/70 |
| 5,839,517 A | * | 11/1998 | Gwinn | B25D 17/043 173/162.2 |
| 8,308,664 B2 | * | 11/2012 | Pathak | G03B 5/00 600/595 |
| 8,468,700 B2 | * | 6/2013 | Wilson | A47G 21/08 30/123 |
| 9,818,310 B2 | * | 11/2017 | Pathak | G09B 19/0092 |
| 9,925,034 B2 | * | 3/2018 | Pathak | A61F 2/08 |
| 9,943,430 B2 | * | 4/2018 | Pathak | A61F 4/00 |
| 2004/0037979 A1 | * | 2/2004 | Monson | F16F 9/04 428/34.1 |
| 2007/0106294 A1 | * | 5/2007 | Nesbitt | A47J 36/025 606/45 |
| 2012/0012732 A1 | * | 1/2012 | Zameroski | B64D 27/26 248/638 |
| 2014/0052275 A1 | * | 2/2014 | Pathak | A61F 4/00 623/65 |
| 2015/0300394 A1 | * | 10/2015 | Pathak | H01H 36/0013 335/205 |
| 2016/0242679 A1 | * | 8/2016 | Pathak | A61B 5/0004 |
| 2017/0211239 A1 | * | 7/2017 | Watkins | E01C 9/086 |
| 2018/0014958 A1 | * | 1/2018 | Pathak | A61F 4/00 |
| 2018/0058536 A1 | * | 3/2018 | Pathak | A47G 21/04 |
| 2018/0168830 A1 | * | 6/2018 | Evans | A61F 2/68 |

OTHER PUBLICATIONS

Steady Spoon manufactured by Performance Health: https://www.performancehealth.com/steady-spoontm.

* cited by examiner

*Primary Examiner* — Sean M Michalski
(74) *Attorney, Agent, or Firm* — Ronald D. Slusky (57) ABSTRACT

An anti-tremor utensil includes an anti-tremor mechanism within a hollow handle. The anti-tremor mechanism includes at least one elastic, fluid-filled ball that isolates tremor-induced motion of handle from the utensil's implement head, e.g., spoon.

19 Claims, 8 Drawing Sheets

ANTI-TREMOR UTENSIL

CROSS-REFERENCE TO RELATED APPLICATION

This application claims the benefit of provisional application Ser. No. 62/359,925 filed Jul. 8, 2016, the disclosure of which is hereby incorporated by reference as though fully set forth herein.

BACKGROUND

People suffering from movement disorders such as essential tremor and Parkinson's disease can find it difficult to use conventional eating utensils because tremors in their hands cause the utensils to shake. It is estimated that there are about 10 million people who have essential tremor and another one million who have Parkinson's disease. This translates to roughly four percent of the American population. Worldwide, there are an estimated 100 million people with hand tremors.

Some users with hand tremors may use a second hand to grab onto the utensil to reduce the tremor, but this is awkward and may not be very effective.

It may be difficult for a person with a significant hand tremor to bring any eating utensil to the mouth, but it is often particularly difficult to use a spoon both because it may be difficult to get food onto the spoon and because food that is on the spoon may get shaken off. Indeed, at least some prior art anti-tremor spoons may not reduce tremors to a sufficient degree to allow persons with particularly strong tremors to use the spoon without a significant amount of food being shaken off.

Utensils are known in the art that include electronics and/or mechanical components that are intended to reduce the shaking of the utensil. Some such anti-tremor utensils are relative expensive, however, and may require a significant amount of maintenance. Anti-tremor utensils that include electronics, moreover, require battery charging, so that users must remember to have them charged so as to be available for use when desired.

For example, the U.S. patent application of Anupam J. Pathak, 20150300394-A1 published Oct. 22, 2015, discloses an anti-tremor spoon comprising a stabilizing handle and an implement attachment. The stabilizing handle comprises two motors, sensors, and a microcontroller which the Pathak application describes as working together to differentiate tremor motions from the intended motions of the user's hands and to counter the unwanted, tremor motions. This is an "active" device in that its sensors respond to the user's tremor and instruct the motors what to do. Experiments that we have conducted suggest that this spoon reduces tremor by only 70 percent, resulting in a great deal of food still being spilled.

Other known anti-tremor spoons are passive, meaning that in contrast to an active device such as described by Pathak, they only respond to mechanical movement of the hand. One such passive device is the "Steady Spoon" manufactured by Performance Health, as shown at https://www.performancehealth.com/steady-spoontm. This device comprises a handle and a gimbal system that separates the user's tremor motions from the part that lifts the food. Advantages of passive devices are that they may be less expensive to manufacture than active devices and do not require the user to remember to charge them. However, the design of the Steady Spoon is such that a user must hold his/her arm in an uncomfortable position when picking up food. Moreover, we have recognized that it is desirable for an anti-tremor spoon to counter six types of motion—translation along the x-axis, y-axis and z-axis, and rotation about each of those axes. However, the Steady Spoon essentially counters only translation along, and rotation around, the main axis of the device.

SUMMARY OF EMBODIMENTS OF THE INVENTION

Particular embodiments of the invention envision an anti-tremor utensil comprising a main shaft to which a utensil head is attached. The utensil head may be a spoon or other eating utensil head. An anti-tremor mechanism of the utensil includes at least one ball at least a portion of which is displaced relative to a support element connected with the main shaft in response to motion of the utensil's handle caused by a user's tremor. The displacement thereby isolates or decouples at least translational hand tremors from the main shaft and thus from the utensil head.

In particular embodiments, the ball may a fluid-filled pouch made of a thin elastic material and in some of those particular embodiments, the ball may be attached at top and bottom areas of attachment to an inside surface of a hollow handle and to the support element, respectively.

In particular embodiments, the support element may be a turntable and rotational motion of the handle caused by a user's tremor may impart such rotational motion to the turntable. The turntable can rotate relative to the main shaft, so that main shaft, and thus the utensil head, are isolated or decoupled from the rotational motion of the handle. In such embodiments, the handle and turntable may be connected by way of a ball as described above so that both translational and rotational tremors can be addressed. Alternatively, in cases where only rotational tremor is desired to be addressed, an element that is more rigid than such a ball could be used instead.

DETAILED DESCRIPTION

With reference to FIGS. 1-9, an anti-tremor utensil 1 embodying the principles of the present invention is seen to include main shaft 40; implement head 10 attached to one end of main shaft 40; counterweight 50—which is encased in a counterweight shell 60 and is attached to a second end of main shaft 40; hollow handle 25; and an anti-tremor mechanism 2 within hollow handle 25. A rectilinear coordinate system that is fixed with respect to handle 25 is also shown in these figures to aid in the description, with main shaft 40 being oriented along the handle's x-axis when the utensil is in an equilibrium state, i.e., without being held or manipulated.

Implement head 10 illustratively comprises a spoon bowl 10a connected to a stem 10b. Implement head 10 is hereinafter referred to as spoon head 10. Spoon bowl 10a may have higher walls than those of a conventional spoon bowl to help reduce any spilling of food that might result from any residual shaking of the utensil. Stem 10b is held within a first end of a sleeve 20 by, illustratively, a friction fit or adhesive. A second end of sleeve 20 is fitted into the utensil's main shaft 40. A pair of magnets 30—one attached to main shaft 40 and the other affixed within sleeve 20—serve as a clip mechanism to detachably secure sleeve 20, and thus spoon head 10, to main shaft 40. The ability to detach spoon head 10/sleeve 20 from the rest of the utensil both facilitates washing of the spoon head and also allows for its replacement by other implement heads, such as a fork or spork.

Figure 6:
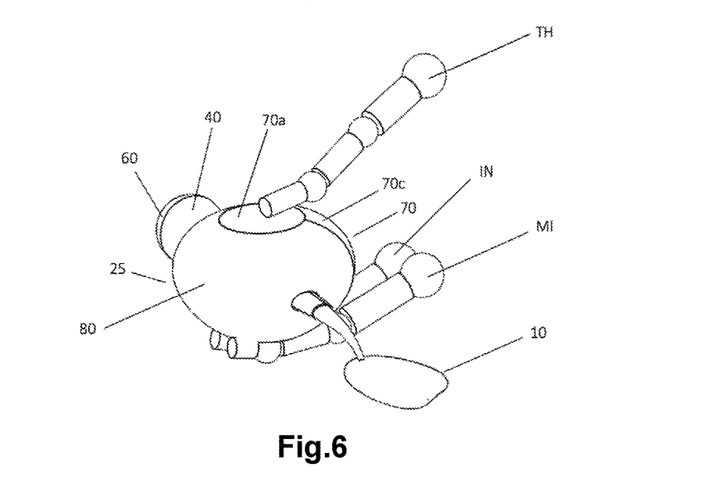
FIG. 6 is a front, top, right perspective view of the utensil, showing stylized representations of fingers holding the utensil.

Hollow handle 25 comprises elastic handle shell 80 and rigid handle shell 70, the latter having top, bottom and middle portions 70a, 70b and 70c, respectively. As shown in FIG. 6, the utensil is designed for a user to grab onto the rigid handle shell 70, with the user's thumb TH placed on handle top 70a and the index and middle fingers, IN and MI, positioned under bottom portion 70b (not visible in FIG. 6). Handle 25 may be of any desired shape that serves the functions for the handle as described herein. It is illustratively an ellipsoid whose outer surface mirrors the "C" shape formed by the user's fingers as shown in FIG. 6.

Main shaft 40 passes through holes 80a and 80b formed in elastic handle shell 80, which is made of elastic material that, in some embodiments, may have properties similar to that of a water balloon, although materials of greater or less elasticity may be found desirable in other embodiments. There will be relative motion between the user's hand and main shaft 40—and thus between the user's hand and spoon head 10—due to the anti-tremor properties of the utensil. That is, spoon head 10 holds relatively still compared to the user's hand tremors. Even though holes 80a and 80b encircle main shaft 40 fairly tightly, handle shell 80, being of an elastic material, can accommodate that relative motion by stretching and/or deforming as the user's hand tremors and shakes rigid handle shell 70. Thus notwithstanding the fairly tight fit of main shaft 40 into handle 25, the tremor imparted to rigid handle shell 70 from the user's hand does not get transmitted to main shaft 40 and thus does not get transmitted to spoon head 10.

The intensity of a user's tremors may be reduced to some extent simply by virtue of the utensil's inertia of rest. Indeed, one function of counterweight 50 is to provide the utensil with additional weight—and thus additional inertia—with the overall utensil weighing approximately 7 oz. in this embodiment, as compared to a conventional stainless-steel eating spoon, which may weigh about 2 oz. Indeed, most of the weight of utensil 1, i.e. the downward force of gravity on the utensil, is distributed to the components that should not oscillate in response to the user's tremors—these including spoon head 10, main shaft 40 and counterweight 50—while using relatively lightweight materials for components that will oscillate—particularly handle 25 and balls 90a and 90b of anti-tremor mechanism 2 described below. This will maximize the effect of reducing tremor without having to make the whole utensil too heavy.

Another function of counterweight 50 is to cause the center of mass of the utensil to be located at the handle 25, allowing the user to grasp the utensil at the center of mass and, at the same time, at a comfortable distance from the spoon head. This mirrors how a conventional spoon is grasped in order to avoid contact between the hand using the utensil and the bowl or food being picked up. Moreover, the anti-tremor properties of the utensil may be most readily achieved when handle 25 is positioned at the center of mass of the utensil.

The fact that a utensil is relatively heavy, however, will typically not be sufficient to keep a utensil steady enough to enable a person with any but the mildest of tremors to hold the utensil steady enough for effective use of the utensil. Rather, in accordance with a feature of the invention, utensil 1 includes anti-tremor mechanism 2, which decouples and/or isolates the tremor motion of the user's hand from main shaft 40, and thus from spoon head 10, so that spoon head 10 tremors to a significantly reduced extent.

In particular, anti-tremor mechanism 2 includes the following elements stacked one on top of one another: Ball 90a; turntable 150; turntable 130 rigidly attached to turntable 150; torsion spring 140 secured between turntables 150 and 130; thrust bearing 110a; washer 120, which is fixed within ring 125 of main shaft 40; thrust bearing 110b, turntable 100 and ball 90b. The cylindrical projection 131 of element 130 extends through holes centered in thrust bearing 110a, ring 125, washer 120, thrust bearing 110b and turntable 100. The bottom 132 of cylindrical projection 131 is substantially flush with the lower surface of turntable 100 and fits into turntable 100 sufficiently tightly that turntables 150, 130 and 100 rotate as a unit about the z-axis. This tight fit is what holds the elements of anti-tremor mechanism 2 together.

Turntable 100 can be thought of as a support element of the utensil since, as discussed in further detail hereinbelow, most of the weight of the overall utensil bears down on ball 90b by way of turntable 100.

Figure 1:
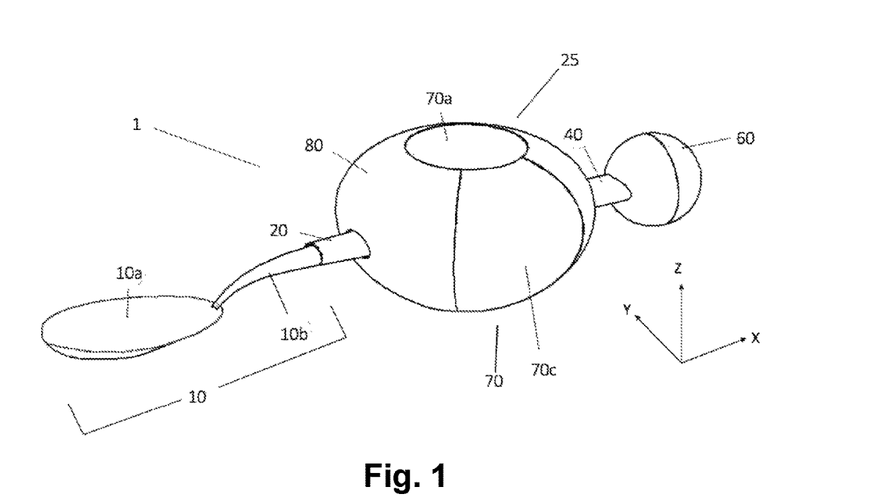
FIG. 1 is a front, top, left perspective view of a utensil embodying the principles of the invention.
Figure 2:
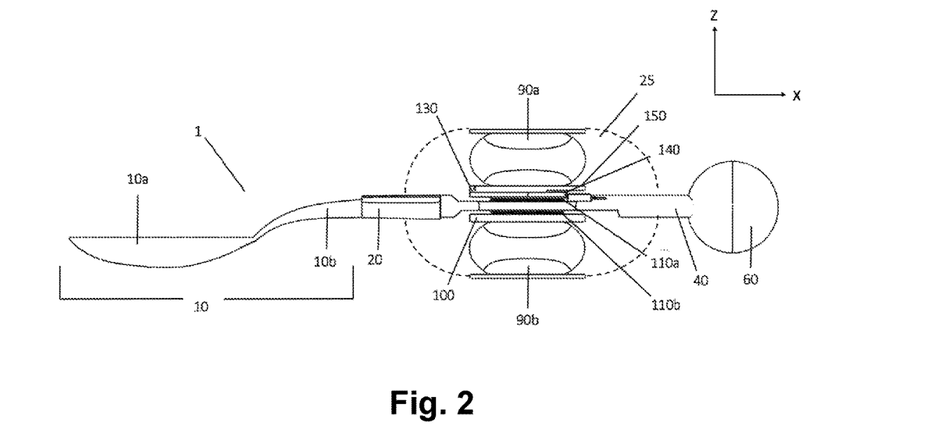
FIG. 2 is a left elevational view of the utensil, with its handle shown in phantom.
Figure 3:
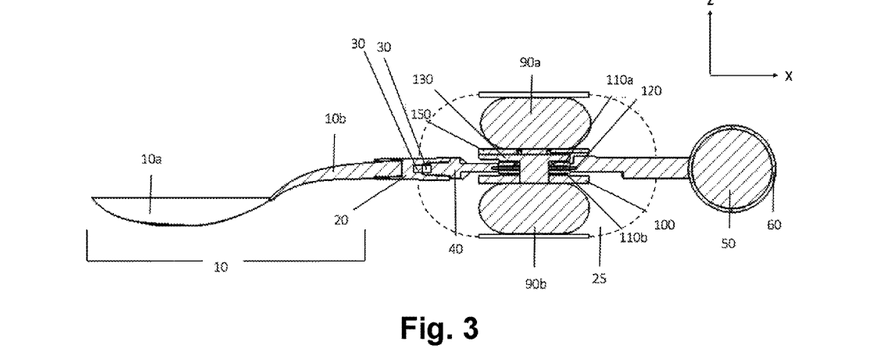
FIG. 3 is a left elevational cross-sectional view of the utensil, with its handle shown in phantom.
Figure 4:
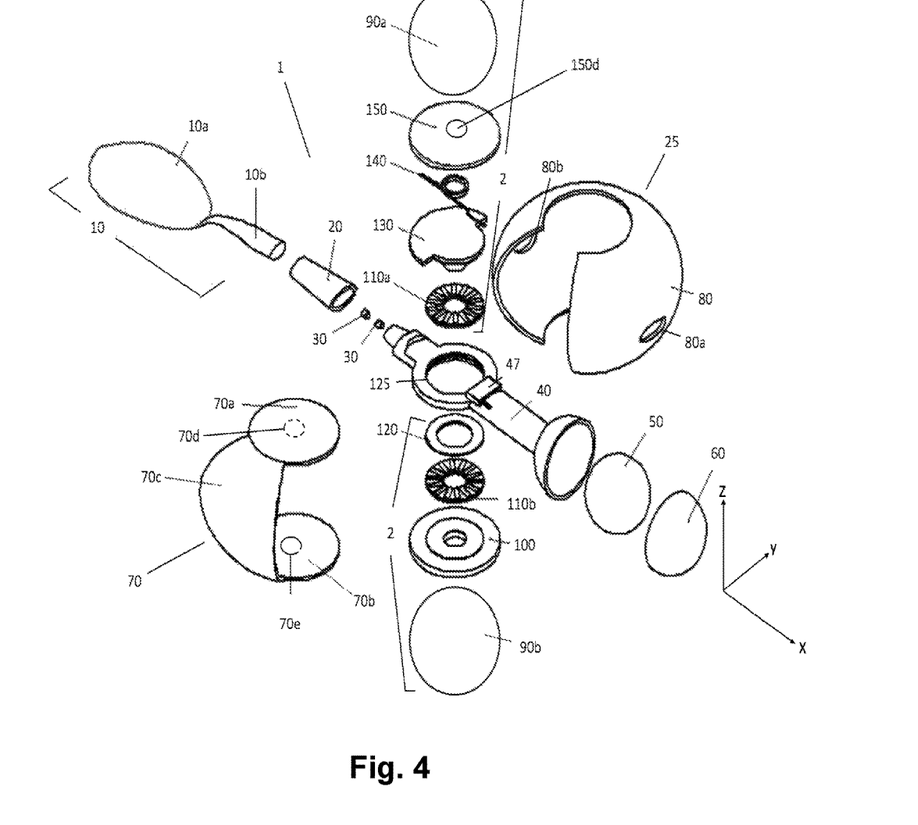
FIG. 4 is a rear, top, left, exploded perspective view of the utensil.
Figure 5:
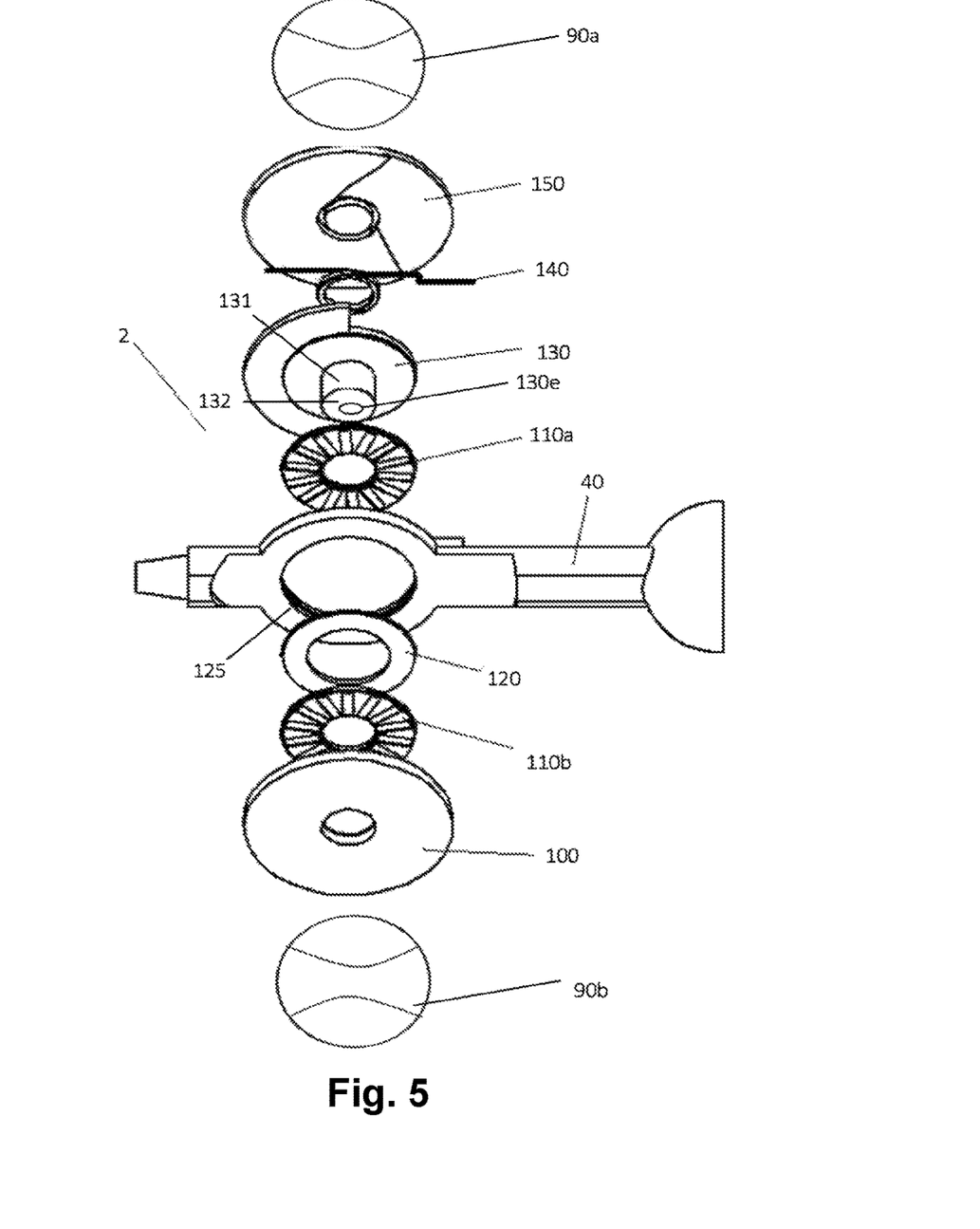
FIG. 5 is a bottom exploded perspective view of the main shaft and anti-tremor mechanism of the utensil.

The raised circular area in turntable 100 as seen in FIG. 4 provides a gap between main shaft 40 and turntable 100. This gap is desirable for turntable 100 to rotate freely relative to main shaft 40.

Balls 90a and 90b are illustratively fluid-filled pouches made of a thin (e.g., 0.002" thick) elastic material such as latex. Balls 90a and 90b are approximately spherical when standing alone. As shown in FIGS. 4 and 6, however, they are deformable and will take on a shape similar to a torus with no hole in response to pressure applied to them once installed within the utensil as seen, for example, in FIGS. 2 and 3. The primary purpose of elastic handle shell is to prevent balls 90a and 90b from being displaced too far from their equilibrium position; without the elastic handle shell 80 being there, the main shaft 40 could slip too far from its equilibrium position relative to handle 25—i.e., far from the position shown in FIGS. 1-3, for example—for the balls 90a and 90*b* to be effective in absorbing the forces generated by the tremor motions of the hand. Elastic handle shell 80 is also responsible for closing off the anti-tremor mechanism 2 from water, dirt or other debris that could hamper the anti-tremor mechanism's effectiveness. Elastic handle shell 80 also serves the aesthetic purpose of hiding the internal components of the anti-tremor mechanism 2 from view.

A user's hand can impart any of six types of motion to handle 25, these being translation along the x-axis, y-axis and z-axis, and rotation about each of those axes. Each type of motion can be positive or negative. Thus, overall, there can be positive and negative translation along the z-axis, which can be thought of as "up and down"; positive and negative translation along the x-axis, which can be thought of as "backward and forward"; positive and negative translation along the y-axis, which can be thought of as "left and right"; positive and negative rotation about the z-axis (clockwise and counter-clockwise rotation as viewed by looking down onto the utensil along the z-axis; positive and negative rotation about the x-axis (clockwise and counter-clockwise rotation as viewed by looking along the utensil from counterweight 50 to spoon head 10 along the x-axis; and positive and negative rotation about the y-axis (clockwise and counter-clockwise rotation as viewed by looking at utensil 1 from the side as in, for example, FIG. 2 along the y-axis.

Among the above-mentioned directions of motion, those that are the most pronounced during tremor are translation along the x- and y-axes, i.e. translation in the x-y plane, and rotation about the z-axis. In addition to the possibility of tremor in those directions (as well as other directions) being reduced by virtue of the utensil being relatively heavy, as noted above, translation in the x-y plane and rotation about the z-axis are significantly reduced by virtue of anti-tremor mechanism 2 embodying the principles of the invention.

In particular, tremor that displaces handle 25 forward and backward along the x-axis and/or left and right along the y-axis results in at least respective portions of balls 90*a* and 90*b* being translated or displaced in the direction of motion across the surface of turntables 150 and 100, respectively. Turntables 150 and 100 do not turn to a significant, if any, extent in response to such translation or displacement of balls 90*a* and 90*b* but, rather, serve simply as surfaces along which balls 90*a* and 90*b* get transported or displaced. Their actual turntable function is discussed hereinbelow.

Figure 7A:
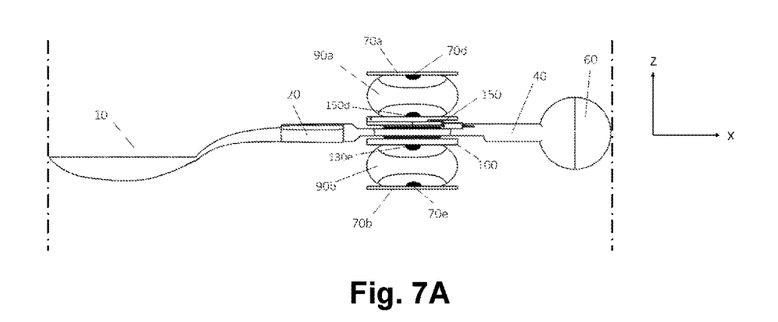
FIG. 7A is a left elevational partial cutaway view of the utensil.
Figure 7B:
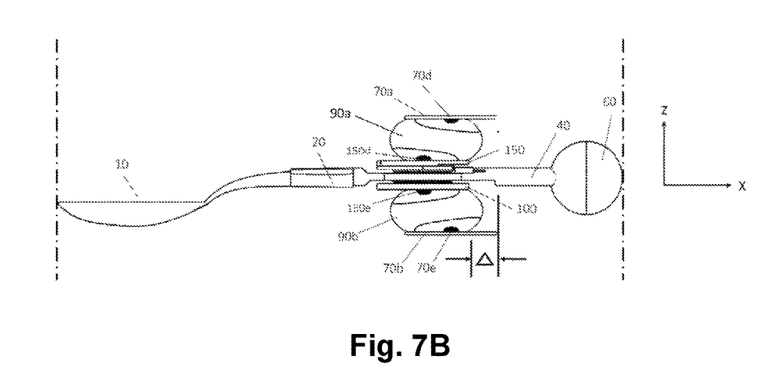
FIG. 7B is a left elevational partial cutaway view of the utensil illustrating the movement of balls of the utensil's anti-tremor mechanism in response to tremor in the x-y plane and, in particular, along the x-axis in this example.

The foregoing is illustrated in FIGS. 7A and 7B for the case of motion in the backward, or positive-x, direction. (Elastic handle shell 80 is not shown in these FIGS and in FIG. 7C to more clearly show elements of anti-tremor mechanism 2.) In particular, FIG. 7A depicts handle 25 at rest, and FIG. 7B depicts handle 25 having been displaced by a user's tremor in the backward, i.e. positive-x, direction by a distance 4. Ball 90*a* is affixed with adhesive to rigid handle shell top 70*a* at small attachment area 70*d*, and to turntable 150 at small attachment area 150*d*. Ball 90*b* is affixed with adhesive to rigid handle shell bottom 70*b* at small attachment area 70*e* and to lower surface 132 of turntable 130's projection 131—which surface, as noted above, is flush with the lower surface of turntable 100—at small attachment area 130*e*. Due to the tight fit of projection 131 within the hole in the center of turntable 100, its bottom surface 132 essentially serves as a central bottom surface of turntable 100 and thus ball 90*b* attached to bottom surface 132 is, for practical purposes, attached to the bottom of turntable 100. As a consequence of this arrangement, the backwards displacement of rigid handle shell 70 causes balls 90*a* and 90*b* to deform such that their surfaces are displaced along the surfaces of turntables 150 and 100, respectively.

The term "utensil body" is introduced at this point as referring to all of utensil 1 except for handle 25 and balls 90*a* and 90*b*. Note, then, that notwithstanding the forward motion of rigid handle shell 70 and the consequent deformation of balls 90*a* and 90*b*, the utensil body moves very little because of its much larger mass, and thus much larger inertia of rest as compared to the mass and inertia of rest of handle 25 and balls 90*a* and 90*b*. It is in this way that the forward motion imparted to handle 25 by the user's hand is decoupled or isolated from the utensil body and, in particular, spoon head 10, which is a part thereof.

Balls 90*a* and 90*b* will deform in a similar way in response to tremors in the negative-x direction, as well as in response to tremors in the positive-y and negative-y directions. Balls 90*a* and 90*b* will also deform in response to tremors that have both an x and y component.

It is thus seen that at least a substantial amount of any tremor-induced translational motion of handle 25 in the x-y plane (to which the utensil body is substantially parallel) does not get transferred to turntables 100 and 150 and thus does not get transferred to the rest of the utensil body including, in particular, spoon head 10, notwithstanding the motion of handle 25. That is to say, spoon head 10 is substantially isolated or decoupled from tremor-induced translational motion of handle 25 in the x-y plane and thus spoon head 10 moves very little notwithstanding such translational motion of handle 25.

Balls 90*a* and 90*b* are attached to the surfaces above and below them at the attachment areas 70*d*, 150*d*, 70*e* and 130*e* in order to keep them in place. Otherwise, balls 90*a* and 90*b* may "wander" away from that central position with a resultant impairment of the anti-tremor function of the utensil. As a result of those attachments, balls 90*a* and 90*b* cannot freely "roll" in the strict sense of that word, i.e. in the same way as a completely untethered ball might roll across a surface. Rather balls 90*a* and 90*b* get temporarily deformed in such a way, as can be appreciated from FIG. 7B, that portions of the surfaces of balls 90*a* and 90*b* a) that were not initially in contact with the adjacent surfaces do become in contact therewith, and b) that portions of the surfaces of balls 90*a* and 90*b* that initially were in contact with the adjacent surfaces become not in contact therewith. In this sense it may be said that balls 90*a* and 90*b* "track" along the adjacent surfaces somewhat analogously to the way in which the linked belt of a bulldozer tracks along the ground.

The areas of attachment 70*d*, 150*d*, 70*e* and 130*e* are preferably small enough to allow the balls 90*a* and 90*b* to deform in an amplitude range that is at least as great as the expected amplitude of the user's hand tremor.

In particular embodiments, middle portion 70*c* of rigid handle shell 70 is rigid enough to prevent any significant squeezing of balls 90*a* and 90*b* when the user grasps handle 25. Such squeezing may be undesirable to the extent that it may over-stretch the elastic walls of the balls 90*a* and 90*b* and thus create too much tension within the elastic walls of the balls 90*a* and 90*b*. This excess of tension may in turn reduce the slack that is desirable to enable the ball walls to deform and thus to isolate from the utensil body movement of rigid handle shell 70 imparted thereto from a user's tremoring. Such a lack of slack and excess of tension would effectively make balls 90*a* and 90*b* be solid structures that transmit the forces generated by the tremoring hand instead of absorbing them.

We turn now to the turntable function of turntables 150, 130 and 100. Turntables 100, 130 and 150 are rigidly connected to one another, as discussed above and thus rotate as a unit. The turntable assembly that includes the three turntables, thrust bearings 110a and 110b and washer 120 act to isolate, or decouple, tremor-induced-rotation of handle 25 about the z-axis from the remainder of utensil body and thus, in particular, from spoon head 10.

In particular, a rotating or twisting motion of handle 25 about the z-axis imparts a rotating or twisting motion to balls 90a and 90b by virtue of their attachments at attachment areas 70d and 70e, respectively. Balls 90a and 90b, in turn, impart a rotating or twisting motion to the turntable assembly by virtue of their attachments at attachment areas 150d and 130e on turntables 150 and 100, respectively. Thrust bearings 110b and 110a, which illustratively are roller bearings, have a relatively low-friction interface with turntables 100 and 150, respectively, as well as with washer 120, which may be made of a highly polished metal. This allows the turntable assembly to readily rotate while imparting only a relatively small amount of rotational force to the remainder of the utensil body and, in particular, to spoon head 10 thereof. In other embodiments, the thrust bearings could be disks or the like made of a low-friction material such as polytetrafluoroethylene.

There is some small amount of residual friction, of course, between thrust bearings 110a and 110b and the surfaces that they interface with. As a result, a twisting motion of handle 25 during a given tremor pulse may tend to rotationally displace the utensil body and thus, in particular, spoon head 10, in the direction of twist to some extent. The subsequent twisting motion of handle 25 in the opposite sense during the subsequent tremor pulse will tend, to some extent, to rotationally displace the utensil body back to its original orientation. Thus, there may be some residual amount of oscillation of spoon head 10 about the z-axis, but it will be relatively small and certainly much less than would occur if all of the twisting motion of the user's tremor were transferred to the spoon head. That is to say, in summary, that components of the user's tremor that twist handle 25 about the z-axis and that therefore cause a rotation of handle 25, balls 90a and 90b and the turntable assembly are, to a significant extent, prevented from being transferred to the remainder of the utensil body and thus spoon head 10. The latter thus tends to remain oriented substantially as it was in the presence of such rotational components of the user's tremor.

Torsion spring 140 is a rotational restoration component that is included as a part of anti-tremor mechanism 2 to counteract forces that might otherwise cause the utensil body to take on an orientation that is not aligned with the x-axis, even while the spoon head itself is remaining substantially tremor-free. Such tendency of the utensil body to become non-aligned with the x-axis can be the result of such phenomena as, for example, the user turning handle 25 in a new direction as she uses the spoon and/or changes in orientation of the user's hand relative to the user's arm and/or body as a whole. The presence of torsion spring 140 in the anti-tremor mechanism results in the utensil body and thus, in particular, spoon head 10 being maintained in their equilibrium positions notwithstanding such phenomena, as will now be explained.

Figure 8A:
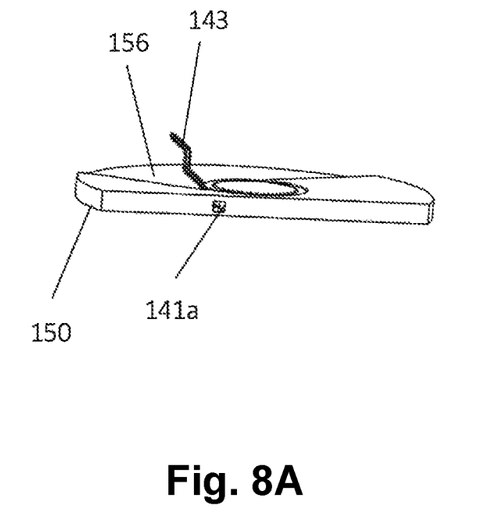
FIG. 8A is a top cross-sectional perspective view of a turntable and torsion spring that form part of the utensil's anti-tremor mechanism.
Figure 8B:
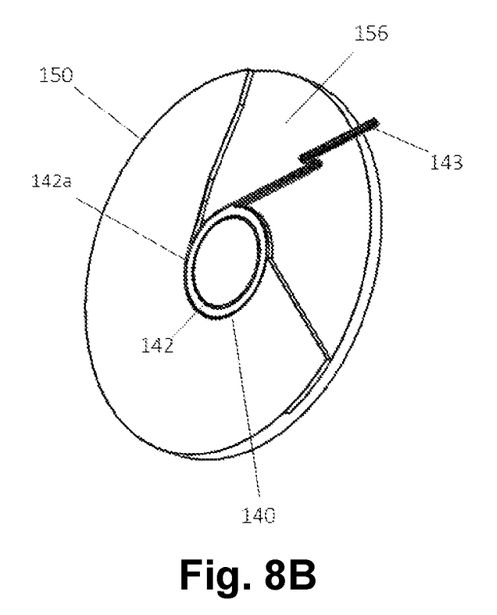
FIG. 8B is top perspective view of the turntable and torsion spring.
Figure 9:
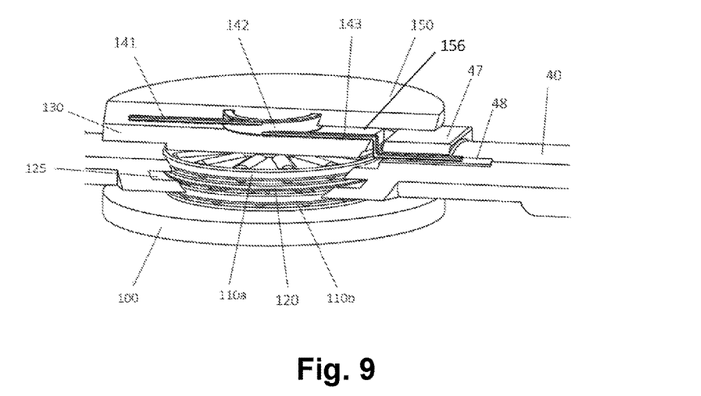
FIG. 9 is a left, top partial cutaway perspective view of a portion of the anti-tremor mechanism.

As shown in FIGS. 8A, 8B, and 9, torsion spring 140 is made up of one or more coils 142 out of which legs 141 and 143 extend. Leg 141 and coils 142 are disposed within linear groove 141a and circular indent or groove 142a, respectively, in the underside of turntable 150. They are anchored in place by virtue of turntables 150 and 130 being glued or otherwise attached together. Leg 143 extends out to main shaft 40 through a wedge-shaped cutout 156 in the underside of turntable 150 and leg 143 is captured at its end in a key groove 48 of a capture housing 47 located on main shaft 40. The presence of cutout 156 allows the turntable assembly comprising turntables 150, 130 and 100 to rotate notwithstanding that leg 143 extends out from coils 142. The absence of cutout 156 would not allow a) leg 143 to fit between 150 and 130, b) assembly 150 and 130 to rotate with respect with leg 143 and thus with respect to main shaft 40.

Because leg 141 is held captured in groove 141a, clockwise (counter-clockwise) rotation of turntable 150 somewhat tightens (untightens) coils 142 against their equilibrium position. Leg 143, held parallel to the axis of main shaft 40 by virtue of being captured underneath housing 47, is free to slide along key groove 48 in response to the tightening and untightening of coils 142. The fact that coils 142 have been tightened (untightened) means that torsion spring 140 exerts a counter-clockwise (clockwise) restoring force on turntable 150—and thus the entire turntable assembly—in response to the turntable being rotated clockwise (counter-clockwise), thereby urging the turntable assembly in a direction opposite to the one in which it was just rotated and thus urging the turntable back to its equilibrium position.

Torsion spring 140 has a smaller natural frequency than the frequency of the typical user's rotational tremor component. For example, the natural frequency of torsion spring 140 is about 1.2 Hz and the rotational component of a hand tremor is typically in the range 4 Hz to 12 Hz As a result of this frequency difference, any tendency of the utensil body to adopt a position that is not aligned with the x-axis is counteracted because when an oscillatory force applied to a spring is at a higher frequency than the natural frequency of the spring, then the amplitude of the oscillation of the spring is less than it would be if the frequencies were the same, and that small amount of oscillation will occur with respect to an equilibrium point of the spring which, in the present case, is with the spring in its rest position, as is desired.

The bottom line is that instead of there being a rotational displacement of the utensil body in response to the phenomena mentioned above, the utensil body experiences a small oscillation (which will die out).

Returning now to balls 90a and 90b, we have found it desirable for ball 90b to be filled with a fluid that is relatively viscous—illustratively having a viscosity similar to that of honey, which is approximately 10,000 centipoises. Having tested materials with various viscosities, we found that a relatively high viscosity for the fluid within ball 90b helps in the isolation or decoupling of the handle's tremor from the utensil body and thus, in particular, spoon head 10. We believe that this may be a consequence of the fact that most of the weight of the overall utensil bears down on ball 90b by way of turntable 100 which can thus be thought of as a support element for the utensil. Thus, most of the force exerted by handle 25 on the rest of the utensil is transferred to ball 90b, with relatively little of that force being transferred to ball 90a. Indeed, we have found that the fluid in ball 90a can have a much lower viscosity than the fluid in ball 90b without much difference in the utensil's anti-tremor performance. In particular embodiments, the viscosity of the fluid in ball 90a may be similar to that of water, e.g., about 1 centipoise.

Having the fluid in ball 90a be of a relatively low viscosity means that, upon being displaced from its neutral position, as shown in FIG. 7B, ball 90a applies a smaller restoring force in the opposite direction to the remainder the anti-tremor mechanism than ball 90b. The latter supplies larger restoring force by virtue of its relatively high viscosity that is needed to support most of the weight of, and thus stabilize, the overall utensil.

Figure 10:
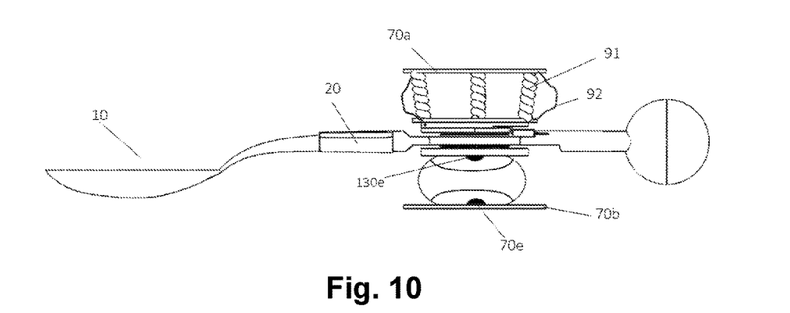
FIGS. 10 and 11 are left elevational partial cutaway views of an alternative embodiment of the utensil.
Figure 11:
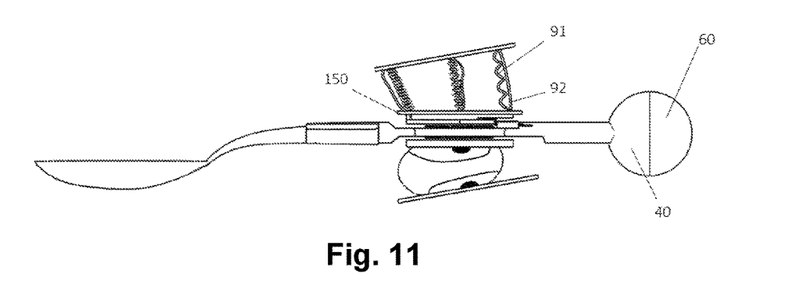

That being said, ball 90a might be replaced with a different mechanism that provides more restoring force than ball 90a itself does, without significantly affecting the anti-tremor functionality of the utensil, given that, as noted above, most of the anti-tremor functionality may largely be being carried out by ball 90b. Such a replacement is shown in the embodiment of FIGS. 10 and 11—in which elastic handle shell 80 and rigid handle middle portion 70c have been removed to more clearly show elements of anti-tremor mechanism 2—wherein the desired restoring force is provided by the three springs 91. The extra restoring force provided by springs 91 can help prevent main shaft 40 from, over time, adopting an awkward angle relative to the user's hand. In such an embodiment, the overall handle might be designed in a such a way that—even while continuing to cover the entire anti-tremor mechanism to, for example, keep out dirt and for aesthetics—the handle does not actually constrain the utensil body in the way that, for example, it is constrained by being inserted through holes 80a and 80b in elastic handle shell 80. In such a case, it thus be desired to provide elements such as strings 92 shown in FIG. 10 as a way of keeping main shaft 40 from falling out of the handle. Strings 92 would have a sufficient length to give enough freedom of motion to the main shaft 40 while preventing it from falling out of the handle.

FIG. 11 shows a situation wherein there has been a counterclockwise rotational tremor pulse around the y-axis. The springs 91 are in the configuration shown while the utensil body is substantially in its original position. The presence of springs 91 will help in restoring the utensil to an equilibrium position.

The natural frequency of this embodiment—that is, the frequency at which the device would oscillate at the highest amplitude in response to an applied oscillatory force—was measured to be 1.6 Hz. The range of frequency for most hand tremors is 4 Hz to 12 Hz. This means that the utensil will not resonate with the user's tremor. When manufacturing, it must be kept in mind that the natural frequency of the utensil should preferably not be in the range of 4 Hz to 12 Hz.

Various materials may be used for each of the various components of the utensil, as will be appreciated by those skilled in the art. In a particular embodiment, the materials may be as follows: balls 90a and 90b—latex of approximate thickness 0.002"; rigid handle 70—plastic; elastic handle shell—latex of approximate thickness of 0.002" or greater, but not as great as 0.02" which, we found, made the elastic handle not pliant enough and caused too much tremor to be communicated to the utensil body; the remainder of the elements—one or more metals.

Utensils embodying the principles of the invention may be produced in various sizes. In a particular embodiment, various ones of the dimensions of the utensil and its components may be as follows:

| | |
|---|---|
| Overall length | 4.18" |
| Height of handle 25 (outside distance between 70a and 70b) | 1.95" |
| Diameter of balls 90a and 90b as installed | 1.50" |
| Height of balls 90a and 90b as installed | 0.69" |
| Radius of turntables 100, 130 and 150 | 0.75" |
| Inside diameter of main shaft center ring 125 | 0.70" |
| Width of main shaft extending from ring 125 | 0.60" |

Each of the FIGS. herein is drawn to scale. Thus, illustrative dimensions of components not explicitly listed above can be determined by scaling measurements of those components taken off the drawings.

The foregoing merely illustrates the principles of the invention and numerous variations from the disclosed embodiments are possible, as will now be discussed.

Figure 12:
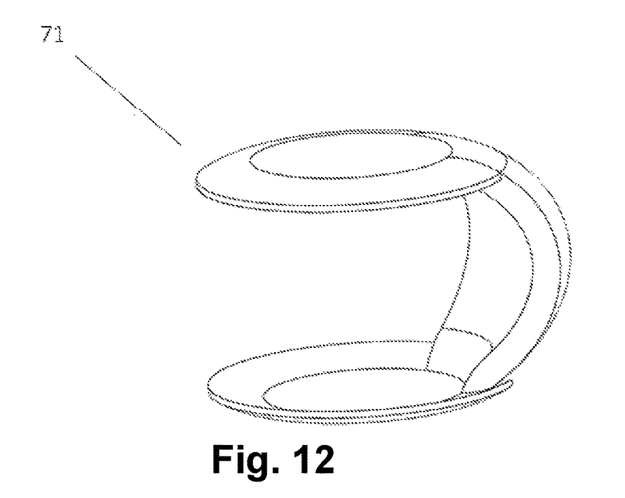
FIGS. 12 and 13 are top, right perspective views of alternatives for the rigid handle shell of the utensil.
Figure 13:
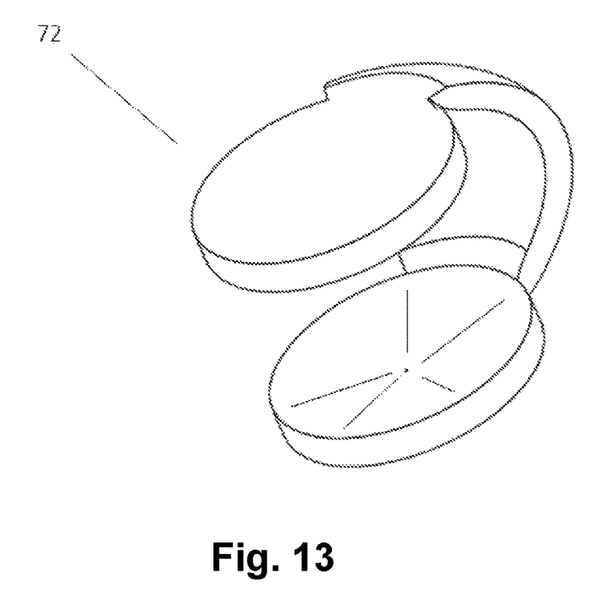

Alternative configurations for the rigid handle shell are shown in FIGS. 12 and 13. Handle shell 71 shown in FIG. 12 has a bowl-shaped bottom and top instead of the flat bottom and top of handle shell 70. Handle shell 72 shown in FIG. 13 has an inverted conical shaped bottom and top. Due to their shape, both of these alternative rigid handle shell configurations impart a restoring force to balls 90a and 90b on a per-tremor-pulse basis in the opposite direction of the balls' motion, the restoring force thus tending to return balls 90a and 90b to their equilibrium positions and thus helping the anti-tremor mechanism to perform optimally. Bowl handle shell 71 is relatively flatter towards the center than the conical handle shell 72. This will give balls 90a and 90b more freedom of motion and only add restoring force as the balls moves closer to the edge of handle shell 71. Yet other geometries for the rigid handle shell may be devised.

Handle shell 80, and thus the entire handle 25, could be made of a rigid material. In that case, however, the holes for main shaft 40 would have to be large enough to accommodate the relative motion between handle 25 and main shaft 40 without main shaft touching the holes' inner rims. Otherwise the user's tremor could, undesirably, be transferred to main shaft 40. Making the holes of such a size that that would not happen, however, might lead to a possibly less aesthetic design and make it easier for dirt and water to get inside the handle. These are among the reasons that making handle shell 80 out of a flexible material and having holes 80a and 80b be as small as practical is probably a better choice.

It was noted hereinabove that middle portion 70c of rigid handle shell 70 is rigid enough to prevent any significant squeezing of balls 90a and 90b when a user grasps handle 25. However, depending on the materials used and other factors and parameters, it may be desirable to design middle portion 70c of rigid handle shell 70 with enough flexibility to enable a user squeezing on top and bottom handle shell portions 70a and 70b to apply enough pressure as to squeeze balls 90a and 90b to an extent sufficient to temporarily arrest their deformation of movement in response to any movement of handle 25. This would effectively create a temporarily rigid utensil that would not isolate the motion of the hand from the utensil body and thus, in particular, from spoon head 10, for as long as such pressure is applied by the user, thereby allowing the user to better scoop up heavy or sticky foods, after which the user would relieve the applied pressure and the anti-tremor properties of the utensil would again be effective. An alternative way of achieving this functionality not requiring the squeezing of the rigid handle shell 70 may be a passive mechanism that reacts to the angle at which the utensil is tilted to keep the entire utensil rigid when it is tilted a certain amount. Such a passive mechanism might be more advantageous for the reason that hard squeezing may cause a person's tremors to intensify.

Balls 90a and 90b can be formed in various shapes, as may be determined by those skilled in the art depending on the intended application, e.g., the expected characteristics of a particular person's tremor.

The magnitude of the allowed displacement of the utensil head and of restoring forces provided by, for example, balls 90a and 90b and springs 91 will vary in various embodiments depending on the particular alternatives used in the utensil's construction including, for example, the use of springs and string rather than balls, the conformation of the rigid handle shell, the materials used for the various components, etc. The balance among these factors may be used in customizing embodiments of the invention for individual users with different tremor frequency and/or magnitude.

In some embodiments, the balls of the anti-tremor mechanism might be attached to only one of the adjacent surfaces or may be not attached to either of the adjacent surfaces, thus being free to roll across those surfaces. Such embodiments might incorporate one or more mechanisms for maintaining the balls' movements centered around an equilibrium location as an alternative to providing areas of attachment to the adjacent surfaces as in the disclosed embodiments.

Counterweight 50 is spherical in shape in the disclosed embodiments. The counterweight may, however, equally well be any other desired shape that is functional. Optimizing the shape, desired total weight of the utensil and aesthetics may yield any number of geometries, positions and materials that may be used to construct the counterweight 50. One design consideration that may lead to the use of a particular shape and/or composition of the counterweight is that it is preferably placed sufficiently far from handle 25 as to avoid the counterweight colliding with the user's hand, causing unwanted oscillations of the utensil.

The distance between the top and bottom surfaces 70*a* and 70*b* of rigid handle shell 70 may vary in various different embodiments so as to accommodate varying users' hand sizes. The lower end of the range of sizes may be bounded, however, by the need for the components of anti-tremor mechanism 2 to be of sufficient size to provide effective anti-tremor functionality.

Rigid handle shell 70 is illustratively smooth on all surfaces. However, in some embodiments it may be textured or grooved with finger patterns to aid a user in holding handle 25. In addition, a strap or the like might be attached to rigid handle shell 70 enabling a user to fasten one or both hands to the utensil.

Various alternative clip mechanisms might be used to attach the sleeve 20 to main shaft 40. The clip mechanism might be, for example, a small extrusion on one wall of the sleeve 20 that clips into an intrusion in the main shaft 40.

Mechanisms other than the use of a torsion spring 140 might be devised to maintain a fixed equilibrium position for main shaft 40. Magnets and/or linear springs might be possibilities.

Lubrication could be added to the inner walls of the elastic handle shell 80 to decrease friction between the elastic handle shell 80 and balls 90*a* and 90*b*.

The principles of the invention are not limited to eating utensils. Rather, we envision that the principles of the invention might be implemented in various utensils and/or tools that are other than eating utensils by which persons with hand tremors may be enabled to carry out tasks that they would otherwise find difficult or impossible. We envision, as but a wide range of possibilities, the use of the invention in a utensil that enables a person with a severe hand tremor to manipulate a key into a lock or to accurately push the buttons of a telephone.

Tremor patterns of particular individuals might be such that only one or the other of a) translation in the x-y plane and b) rotation about the z-axis are particularly strong, in which case, the utensil might include only those elements necessary to address that particular form of tremor. For example, if rotational tremor is not to be dealt with by the anti-tremor mechanism, the element(s) that the ball(s) interface with would not need to have a rotational degree of freedom, i.e. would not need to be turntable(s) but rather, could be totally fixed in relation to the rest of the utensil body. Conversely, something other than elastic balls might be used as the intermediary elements between the handle and the utensil's turntables if translational tremor motion was not to be addressed. Indeed, in cases where the anti-tremor mechanism is relied on substantially only to deal with rotational tremors, the intermediary elements might fixedly connect the handle to the turntables.

It will thus be appreciated that those skilled in the art will be able to devise various alternative arrangements that, although not explicitly shown or described herein, embodying the principles of the invention and thus are within their spirit and scope.

The invention claimed is:

1. An anti-tremor utensil comprising
a utensil body including a support element,
a handle, and
at least a first ball in contact with, and arranged to support, the support element, the ball being configured in such a way a tremor imparted to the handle by a tremoring hand holding the handle will cause a displacement of at least a portion of the ball relative to the support element,
whereby at least a portion of the tremor imparted to the handle is isolated or decoupled from the utensil body.

2. The anti-tremor utensil of claim 1 wherein the ball is further in contact with the an interior surface of the handle.

3. The anti-tremor utensil of claim 1 wherein the weight of the utensil is substantially supported on the ball.

4. The anti-tremor utensil of claim 1 wherein the ball is a fluid-filled elastic pouch.

5. The anti-tremor utensil of claim 4 wherein the fluid has a viscosity substantially greater than 1 centipoise.

6. The anti-tremor utensil of claim 4 wherein the fluid has a viscosity of about 10,000 centipoises.

7. The anti-tremor utensil of claim 1 wherein the displacement is such that a portion of the ball, in response to the tremor, is changed between being in contact with the support element and being not in contact with the support element.

8. The anti-tremor utensil of claim 1 wherein the displacement is such that the ball is translationally displaced on the support element.

9. The anti-tremor utensil of claim 1 wherein the translational displacement isolates or decouples from the utensil body a tremor imparted to the handle in a plane substantially parallel to the utensil body.

10. The anti-tremor utensil of claim 1 wherein the displacement is in a particular direction, and wherein the anti-tremor utensil further comprises one or more elements configured to impart a restoring force to the utensil body in a direction opposite to said particular direction.

11. The anti-tremor utensil of claim 10 wherein the one or more elements configured to impart a further restoring force to the utensil body includes one or more springs connected between the utensil body and an interior surface of the handle.

12. The anti-tremor utensil of claim 1 wherein the displacement is such that the ball is twisted around an axis that is substantially non-parallel to a plane substantially parallel to the utensil body.

13. The anti-tremor utensil of claim 12 wherein the support element is a turntable, and wherein at least one of the ball and the turntable are configured in such a way that the displacement causes a rotation of the turntable.

14. The anti-tremor utensil of claim 13 further comprising one or more rotational restoration components configured in such a way as to impart a rotational restoring force to the turntable in a direction that is substantially opposite to the direction of rotation of the turntable.

15. The anti-tremor utensil of claim 14 wherein the one or more rotational restoration components is a torsion spring.

16. The anti-tremor utensil of claim 1 wherein an area of the ball in contact with the support element is attached to the support element.

17. The anti-tremor utensil of claim 1 wherein an area of the ball in contact with the handle is attached to the handle.

18. The anti-tremor utensil of claim 1 wherein the utensil body further includes a utensil head at a first end of the utensil body.

19. The anti-tremor utensil of claim 18 wherein the utensil body further includes a counterweight at a second end of the utensil body.

* * * * *